(12) United States Patent
Barnes

(10) Patent No.: US 6,794,668 B2
(45) Date of Patent: Sep. 21, 2004

(54) METHOD AND APPARATUS FOR PRINT MEDIA DETECTION

(75) Inventor: Arthur H. Barnes, Battle Ground, WA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 101 days.

(21) Appl. No.: 09/923,115

(22) Filed: Aug. 6, 2001

(65) Prior Publication Data

US 2003/0025092 A1 Feb. 6, 2003

(51) Int. Cl.⁷ .......................... G01N 21/86; G01V 8/00
(52) U.S. Cl. ........................ 250/559.27; 250/223 R; 356/448
(58) Field of Search ............... 250/559.27, 559.28, 250/559.4, 559.11, 559.16, 559.18, 559.39, 223 R; 356/448, 446, 432, 433, 630; 347/104, 105, 106

(56) References Cited

U.S. PATENT DOCUMENTS

| | | |
|---|---|---|
| 4,540,887 A | 9/1985 | Minerd et al. |
| 4,617,580 A | 10/1986 | Miyakawa |
| 4,810,894 A * | 3/1989 | Nagao et al. .......... 250/559.27 |
| 5,047,652 A * | 9/1991 | Lisnyansky et al. ... 250/559.01 |
| 5,119,132 A | 6/1992 | Butler |
| 5,135,321 A | 8/1992 | Olsen et al. |
| 5,139,339 A | 8/1992 | Courtney et al. |
| 5,466,079 A | 11/1995 | Quintana |
| 5,564,848 A | 10/1996 | Quintana |
| 5,764,251 A | 6/1998 | Hashimoto |
| 5,774,146 A | 6/1998 | Mizutani |
| 6,036,298 A | 3/2000 | Walker |

* cited by examiner

Primary Examiner—David Porta
Assistant Examiner—Seung C. Sohn

(57) ABSTRACT

Print media thickness and transmissivity is determined using transmissive light. The light is beamed onto a reflective and absorptive surface. A profile is generated and stored for each predetermined medium. The data stored is used in the manner of a look-up table for comparison to a profile of an unknown type media. Hard copy apparatus multi-pick recognition is also described.

14 Claims, 3 Drawing Sheets

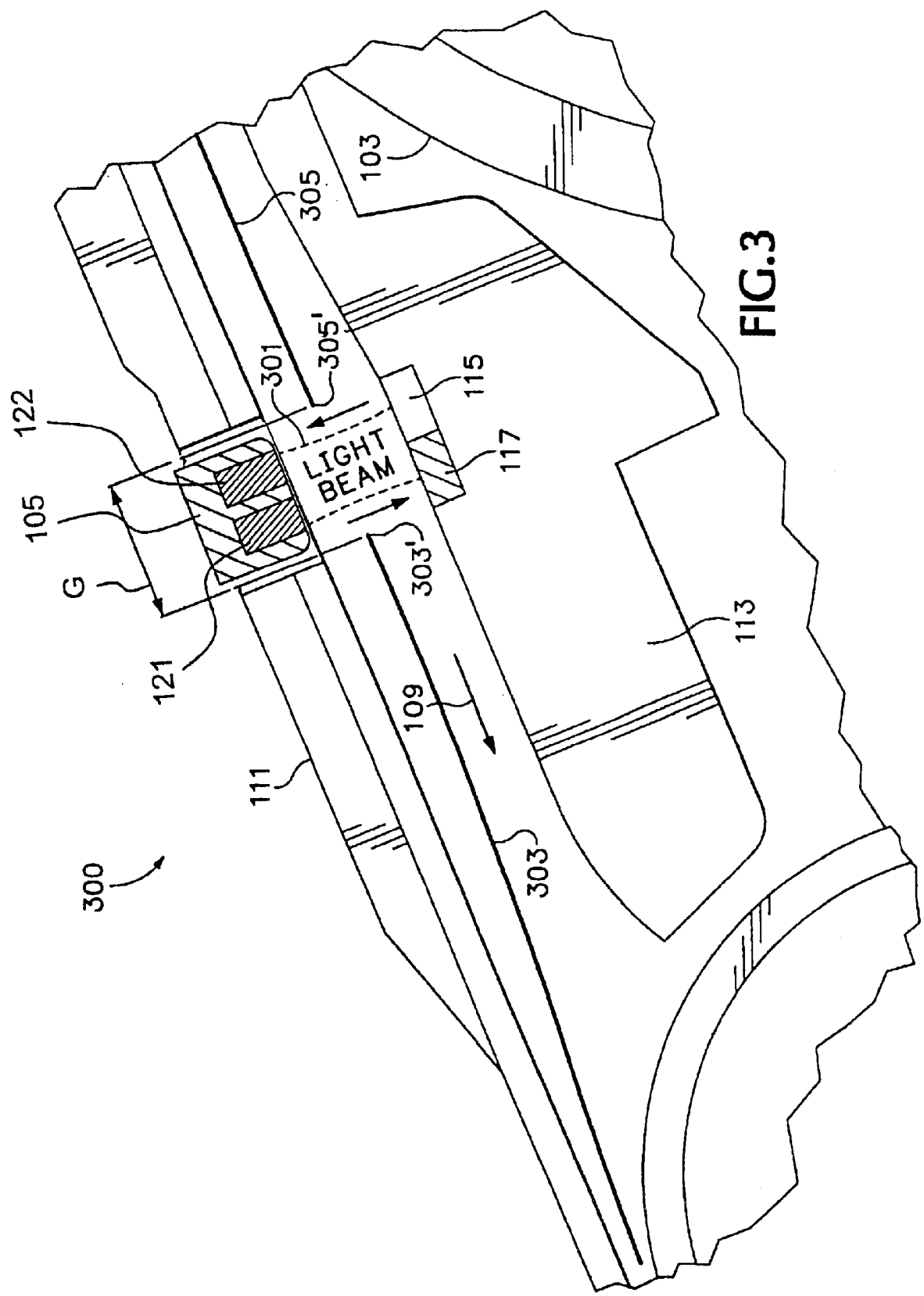

METHOD AND APPARATUS FOR PRINT MEDIA DETECTION

CROSS-REFERENCE TO RELATED APPLICATIONS

Not Applicable.

STATEMENT REGARDING FEDERALLY SPONSORED RESEARCH OR DEVELOPMENT

Not Applicable.

REFERENCE TO AN APPENDIX

Not Applicable.

BACKGROUND OF THE INVENTION

1. Field of the Invention

The present invention relates generally to hard copy apparatus, more particularly to print media sensing, and specifically to an optical sensing method and apparatus for print media sheet recognition.

2. Description of Related Art

In designing paper path for hard copy apparatus, a designer must address the problem of detecting print media (hereinafter referred to generically as "paper," regardless of form, e.g., plain paper, special media, envelopes, and the like as would be common to the state of the art), including type recognition, positioning, multiple sheet picks, and transport to and through the printing zone.

Clearly, knowledge of the type of media currently being printed is an obvious necessity.

Other related printing problems also exist. For example, it is rare that multiple sheet picks present perfectly registered sheets of paper where a printing error—generally print registration on the page—will not occur. When multiple sheets are overlapped, state of the art paper length sensing devices generally indicate a single sheet that is longer than the actual media in the input supply because the commonly used optical detectors or opto-mechanical interrupters inherently do not have the capability to sense the presence of two overlapped sheets of paper since the overlapped region between the two sheets generates the same signal as a single sheet.

Exemplary optical media sensing methods and apparatus are shown in U.S. Pat. No. 5,135,321 (Olsen et al.), U.S. Pat. No. 5,466,079 (Quintana) and its divisional, U.S. Pat. No. 5,564,848 (each assigned to the common assignee herein and incorporated by reference in their entireties). Multiple sheet picks effect a throughput loss as any print is likely to be mis-registered, requiring a reprinting.

Another ADVANCED MEDIA DETERMINATION SYSTEM FOR INKJET PRINTING is described by Walker et al. in U.S. patent application Ser. No. 09/607,206 (a continuation-in-part of Ser. No. 09/430,489, which is a continuation-in-part of Ser. No. 09/183,086, which is a continuation-in-part of U.S. Pat. No. 6,036,298 (incorporated herein by reference). A system of classifying the type of incoming media entering an inkjet or other printing mechanism is provided to identify the media without requiring any special manufacturer markings. The leading edge of the incoming media is optically scanned using a blue-violet light to obtain both diffuse and specular reflectance values. A Fourier transform of these reflectance values generates a spatial frequency signature for the incoming media. The spatial frequency is compared with known values for different types of media to classify the incoming media according to major categories, such as transparencies, glossy photo media, premium paper and plain paper, as well as specific types of media within these categories, such as matte photo premium media and highloss photo media. An optimum print mode is selected according to the determined media type to automatically generate outstanding images without unnecessary user intervention. A printing mechanism constructed to implement this method is also provided.

U.S. patent application Ser. No. 09/470,812 by Barbera et al. for a METHOD AND APPARATUS FOR PRINT MEDIA DETECTION (assigned to the common assignee herein and incorporated by reference) describes a multi-purpose, transmissive paper sensor which includes a light beam projector and light detector having an analog output signal. Changes in the output signal from an open loop condition indicate the presences of at least one print medium being in the field-of-view of the sensor. Output signals indicative of print media leading edge, trailing edge, and number of sheets interrupting the light beam provide improved print media transport control for hard copy apparatus.

It has been determined that there are additional criteria by which media can be characterized.

BRIEF SUMMARY OF THE INVENTION

In accordance with the present invention, media thickness and transmissivity are used to increase media detection accuracy. Additionally, the present invention can be used to determine if there has been a multi-pick at the input supply.

In its basic aspect, the present invention provides a method for identifying an unknown print medium, the method including: recording data representative of medium thickness and transmissivity using an incident light source; and comparing recorded data from said recording to predetermined data representative of known print medium thickness and transmissivity, In another aspect, the present invention is a method for characterizing print media including: beaming transmissive light through a first type of print medium; impinging the light onto surface reflective of the light and a surface absorptive of the light; recording a profile representative of light reflection and light absorption; and storing said profile in a memory with an identifier associated with said first type of print medium.

In another aspect, the present invention provides a method for determining a multi-pick feed of cut sheet print media, the method including: storing first data representative of media thickness and transmissivity of a single in sheet of a known print medium; storing second data representative of media thickness and transmissivity of at least two stacked sheets of a known print medium; recording third data representative of current medium thickness and transmissivity during transport of said current medium from a supply toward a printing zone; and comparing said third data to said first and second data.

In yet another aspect, the present invention provides a print media sensor device, including: mounted for bracketing a print media transport path, emitter—receptor means for directing a light beam across the transport path, the light beam having predetermined intensity and wavelength for penetrating print media; and aligned with the emitter means such that said light beam is received after passing through a sheet of print media in said path, an associated light absorbing means and an associated light reflecting means for receiving the light beam, wherein the receptor means provides an output signal indicative of thickness and transmissivity of the sheet.

In still another aspect, the present invention is a computer memory including: computer code for recording data representative of print medium thickness and transmissivity using an incident light source; and computer code for comparing recorded data from said recording to predetermined data representative of known print medium thickness and transmissivity.

The foregoing summary is not intended to be an inclusive list of all the aspects, objects, advantages and features of the present invention nor should any limitation on the scope of the invention be implied therefrom. This Summary is provided in accordance with the mandate of 37 C.F.R. 1.73 and M.P.E.P. 608.01 (d) merely to apprise the public, and more especially those interested in the particular art to which the invention relates, of the nature of the invention in order to be of assistance in aiding ready understanding of the patent in future searches. Other objects, features and advantages of the present invention will become apparent upon consideration of the following explanation and the accompanying drawings, in which like reference designations represent like features throughout the drawings.

BRIEF DESCRIPTION OF THE DRAWINGS

FIG. 3 is a detail schematic drawing in elevation view of an alternative embodiment of the present invention as shown in FIG. 1.

The drawings referred to in this specification should be understood as not being drawn to scale except if specifically annotated.

DETAILED DESCRIPTION OF THE INVENTION

Reference is made now in detail to a specific embodiment of the present invention, which illustrates the best mode presently contemplated for practicing the invention. Alternative embodiments are also briefly described as applicable.

Figure 1:
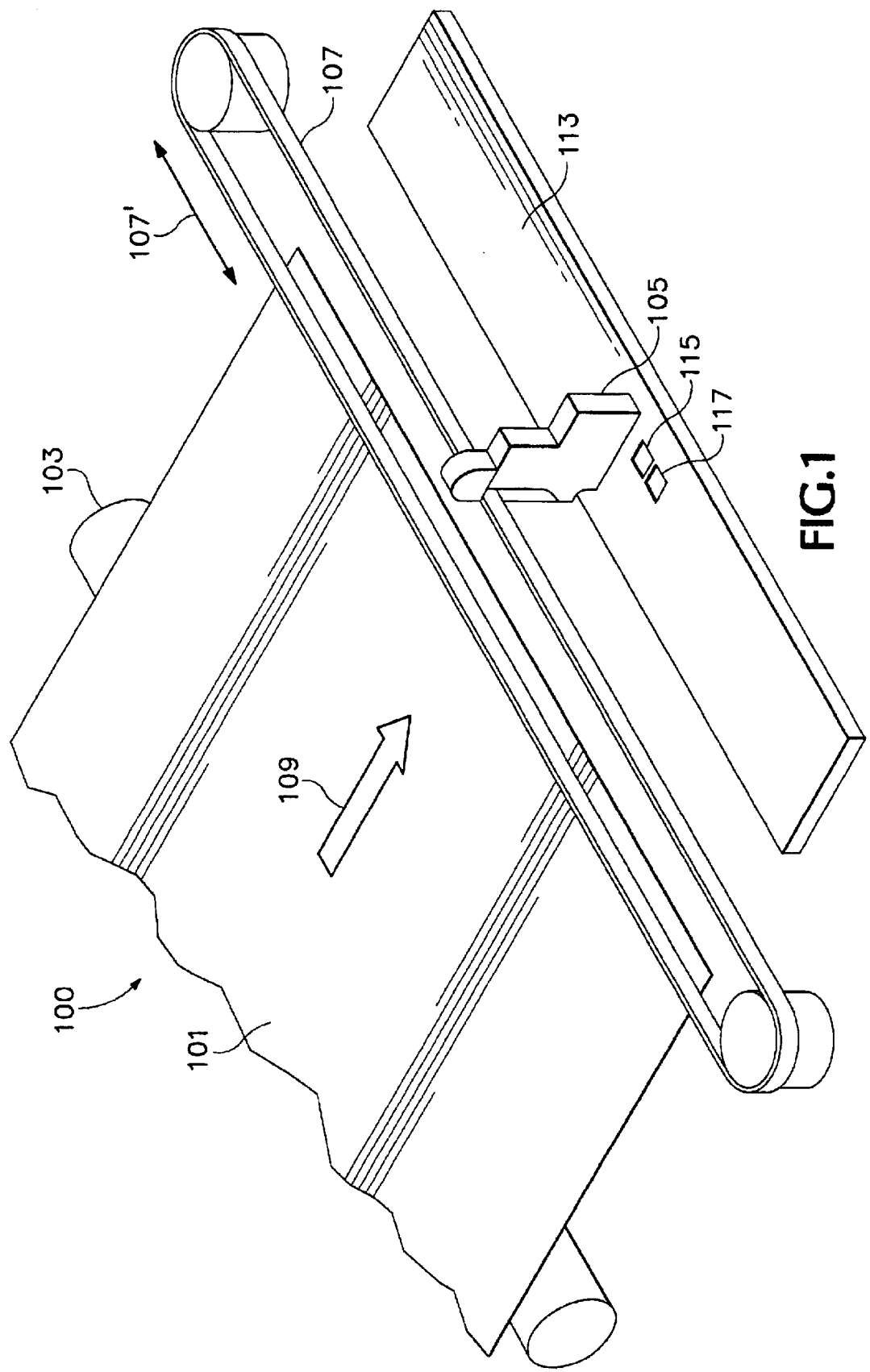
FIG. 1 is a schematic illustration of the present invention in a partial apparatus perspective view.

Turning to FIG. 1, an apparatus 100 in accordance with the present invention is demonstrated. A transport mechanism 103 brings a sheet 101 of print media from a supply (e.g., an input tray stack, not shown). Along the paper path 109 (represented by an arrow), generally referred to in the art as the Y-axis, an optical sensing device 105 is mounted for transport (reciprocal motion is represented by an arrow 107'). In this embodiment, the device 105 is transported on a suitably mounted and powered, bidirectional, endless loop belt 107 in a scanning axis, generally referred to in the art as the X-axis, across the paper path 109. The optical sensing device, or transmissive type "paper sensor," 105 can be of a type that is commercially available, e.g., model SFH9500 manufactured by Siemens corp. The Walker et al., supra, devices describe a blue light device which can also be employed; e.g., model GP1S522 manufactured by Sharp Electronic Components, Sharp corp. Such sensors have a light emitter and light detector as would be known in the art. The paper sensor 105 is preferably positioned in a linear transport region of the paper path 109.

A lower paper guide, or pivot 113 is positioned in the paper path 109 and subjacently to the scanning paper sensor 105 such that the sheet 101 passes between the two. The lower paper guide 113 includes a reflective element 115, such as a mirror, and a non-reflective (light absorptive) element 117, e.g., a black plastic or rubber insert. It will be recognized by those skilled in the art that the exact implementation will be dependent upon the wavelength of transmitted light from the paper sensor 105.

Turning to the alternative embodiment of FIG. 3, it will also be recognized by those skilled in the art that the transmissive sensor 105 and associated reflective 115 element and absorptive element 117 can be built into upper and lower paper guides 111, 113, respectively, in the paper path 109 of a hard copy apparatus structure 300 (or be mounted elsewhere upstream of the printing zone of the hard copy apparatus). Memory 100 is shown connected to transmissive sensor 105. Line 303 represents a leading sheet of media and line 305 represents a trailing sheet of media having been brought to this stage of the input paper path 109 by the transport mechanism 103 (in fact, the sheets are in at least partial contact with the guides 111, 113). No paper is in the light beam 301 and the full intensity of the light hits the reflecting element 115 and absorptive element 117 associated with the sensor 105 when a sensor-size defined gap "G." between a first sheet 303 (having a trailing edge 303') and a second sheet 305 (having a leading edge 305') in the paper path 109 passes the sensor.

In operation, a sheet 111 (FIG. 1) or 303, 305 (FIG. 3) of media is scanned with a light beam 301 (FIG. 3 only) from the sensor 105 (actively as in FIG. 1 or passively as in FIG. 3) while the sheet is over the reflective element 115 and the absorptive element 117. The gain in amplitude and the shape of the response is recorded for many known types of media and a profile for each is stored in memory. The media thickness and transmissivity are properties of the media type and thus can be used for identification purposes.

Figure 2:
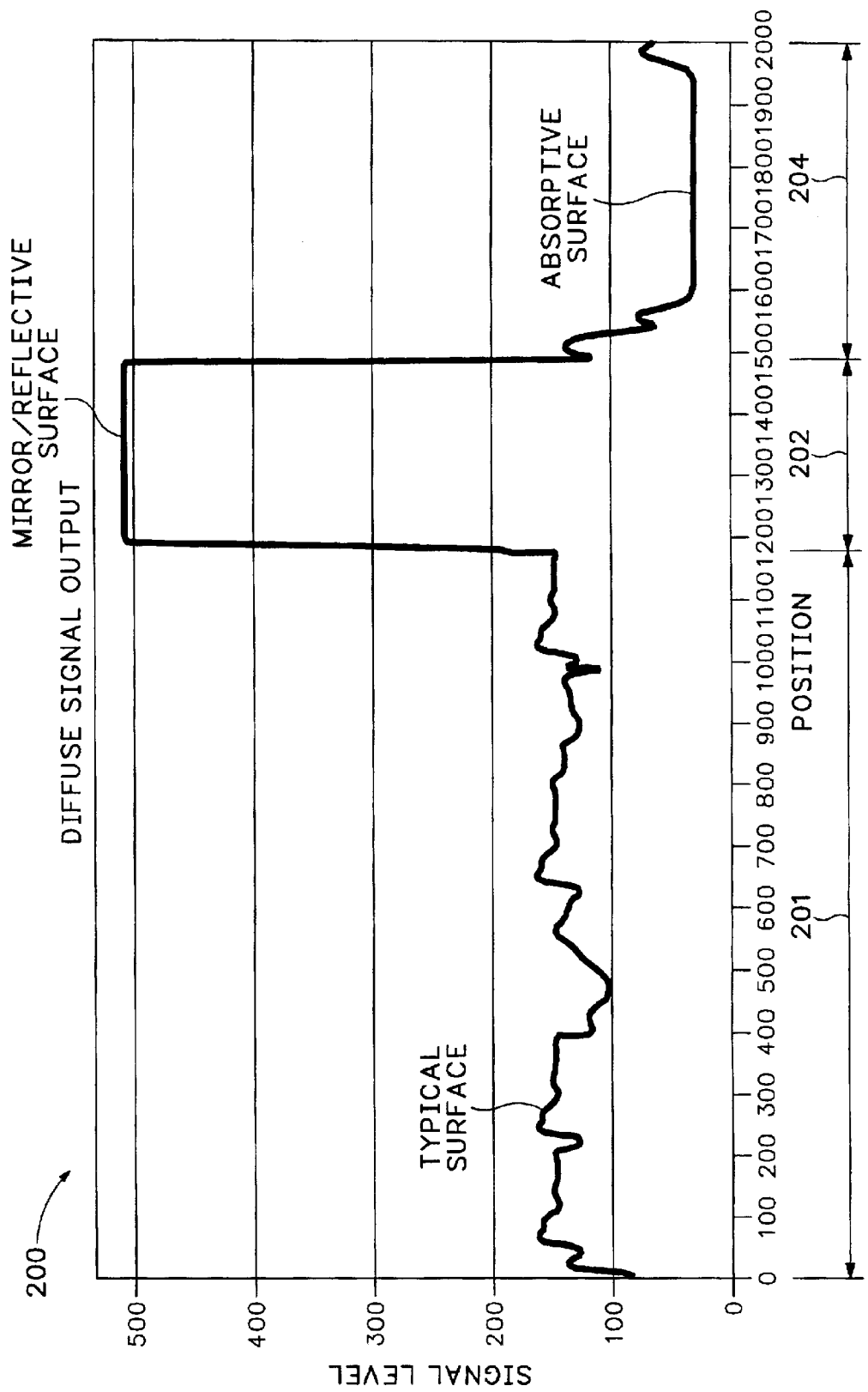
FIG. 2 is a graph showing a function of a diffuse signal level as it passes across an apparatus paper guide, or pivot, and through media transported across reflective and absorptive surfaces in accordance with the present invention as shown in FIG. 1.

Turning to FIG. 2, an exemplary media response profile 200 is illustrated. This profile 200 was generated experimentally using the Walker et al., supra, devices, shining a beam of light having a wavelength of approximately 428 nm at about 850 $\mu$W/steradian. The media type scanned was 20 lb., blank, copy paper. The abscissa (horizontal) is in units of position, e.g., $\frac{1}{600}$ths inch (viz., dpi resolution), and the ordinate is in units for signal level, e.g., millivolts. In region 201 what is exhibited is the sensor 105 reaction to illuminating the lower platen ("typical surface"), or pivot, 113.

In region 202 the response of the sensor 105 over the reflective element 115 shows that as the sensor field-of-view (x=~1175) reaches the reflective surface, the diffuse signal begins to climb until the entire field-of-view encompasses the reflective element. Allowing for this lag, the signal peaks.

Then, as the field-of-view edges over the reflective surface and onto the lower guide 113, the signal returns to approximately the first value. In other words over any pivot region between the reflective and absorptive elements 115, 117, as shown in FIG. 1, the signal drops to the approximate level in region 201. Thus, in such a region the signal level response is the same as in region 201.

In region 204, the sensor field-of-view encounters the absorptive element 117. The signal level drops below the "typical surface" value until sometime thereafter when the sensor 105 again encounters the pivot surface.

A set of profiles is generated for each type of print media commonly used with a particular hard copy apparatus. The profiles are stored in a memory (not shown) as would be known in the art and be usable as a look-up table (LUT).

When a media sheet 111 of an unknown type is being used, a profile is generated. The profile of the unknown media is compared to the profiles in the LUT. If a match is found, the hard copy apparatus controller (not shown) adjusts the printing characteristics accordingly. If no match is found, the new profile is labeled and added to the LUT.

An implementation employing a plurality of emitters and detectors may also be constructed.

An implementation computerized program is provided as part of the hard copy apparatus or as part of a manufacturing tool for generating print medium profiles. The program can be in software or on-board a hard copy apparatus as a firmware routine. The program requires code for simply activating the sensor 105, running a sheet 111 of the media to be characterized through the paper path 109 while recording a profile, and storing the new profile with an identifier label—e.g., "HP™ PhotoSmart™ glossy"—in the LUT.

Multi-pick situations are also identifiable. Using specific media, readings are stored using at least two sheets over the reflective and absorptive elements 115, 117. The data is stored in the LUT. During normal operation, each pick can be analyzed upstream of a printing zone. If a multi-pick is recognized, the transport 103 can be reversed, returning the sheets to the supply and another pick attempted.

Known manner electronic controls and memory (not shown) generally associated with hard copy apparatus are used for controlling the elements of the present invention and firmware or software associated with the operational process.

The foregoing description of the preferred embodiment of the present invention has been presented for purposes of illustration and description. It is not intended to be exhaustive or to limit the invention to the precise form or to exemplary embodiments disclosed. Obviously, many modifications and variations will be apparent to practitioners skilled in this art. Similarly, any process steps go described might be interchangeable with other steps in order to achieve the same result. The embodiment was chosen and described in order to best explain the principles of the invention and its best mode practical application, thereby to enable others skilled in the art to understand the invention for various embodiments and with various modifications as are suited to the particular use or implementation contemplated. It is intended that the scope of the invention be defined by the claims appended hereto and their equivalents. Reference to an element in the singular is not intended to mean "one and only one" unless explicitly so stated, but rather means "one or more." Moreover, no element, component, nor method step in the present disclosure is intended to be dedicated to the public regardless of whether the element, component, or method step is explicitly recited in the following claims. No claim element herein is to be construed under the provisions of 35 U.S.C. Sec. 112, sixth paragraph, unless the element is expressly recited using the phrase "means for . . . " and no process step herein is to be construed under those provisions unless the step or steps are expressly recited using the phrase "comprising the step(s) of . . . ."

What is claimed is:

1. A method for identifying an unknown print medium, the method comprising:

transporting a print medium along a paper path relative to a paper guide, the paper guide positioned subjacently to a transmissive sensor and supporting a reflective element and a non-reflective element in a stationary position relative to the transmissive sensor;

beaming tranamissive light through the print medium;

impinging the transmissive light onto the reflective element;

impinging the transmissive light onto the non-reflective element;

sensing a reflected light from the reflective element and the non-reflective element;

recording data representative of light reflection and light absorption; and comparing recorded data from said recording to predetermined data representative of a known print medium thickness and a known print medium transmissivity.

2. The method as set forth in claim 1 wherein the step of recording data representative of light reflection and light absorption further comprises:

recording transmissive light levels of the print medium over a lightwave reflective element, and recording transmissive light levels of the print medium over a lightwave absorptive element.

3. The method as set forth in claim 1 further comprising:

when no match between said recorded data and said predetermined data is obtained, storing said recorded data as a new print medium data file.

4. The method as set forth in claim 1 embodied in computer code.

5. A method for characterizing print media comprising:

transporting a print medium along a paper path relative to a paper guide, the paper guide positioned subjacently to a transmissive sensor and fixedly supporting a reflective element and a non-reflective element relative to the transmissive sensor;

beaming transmissive light though the print medium;

impinging the transmissive light onto a surface reflective of the transmissive light and a surface absorptive of the transmissive light;

recording a profile representative of light reflection and fight absorption of the print medium; and storing said profile in a memory with an identifier associated with said print medium.

6. The method as set forth in claim 5 further comprising:

beaming the transmissive light through a second type of print medium;

impinging the transmissive light onto the surface reflective of the transmissive light and the surface absorptive of the transmissive light;

recording a profile representative of light reflection and light absorption of the second type of print medium; and storing said profile in the memory with an identifier associated with said second type of print medium.

7. The method as set forth in claim 6 further comprising:

beaming the transmissive light through a third type of print medium;

impinging the tranamissive light onto the surface reflective of the transmissive light and the surface absorptive of the transmissive light;

recording a profile representative of light reflection and light absorption of the third type of print medium; and referencing said memory as a look-up table for identifying the profile of the third type of print medium.

8. A method for characterizing print media comprising:

transporting a print medium along a paper path of a hard copy apparatus structure including a lower paper guide including a reflective element and a non-reflective element, the lower paper guide positioned subjacently to a transmissive sensor;

beaming transmissive light through the print medium;

impinging the transmissive light onto a surface reflective of the transmissive light and a surface absorptive of the transmissive light;

recording a profile representative of light reflection and light absorption of the print medium;

storing said profile in a memory with an identifier associated with said print medium;

beaming the transmissive light through a second type of print medium;

impinging the transmissive light onto the surface reflective of the transmissive light and the surface absorptive of the transmissive light;

recording a profile representative of light reflection and light absorption of the second type of print medium;

storing said profile in the memory with an identifier associated with said second type of print medium;

beaming the transmissive light through a third of print medium;

impinging the transmissive light onto the surface reflective of the transmissive light and the surface absorptive of the transmissive light;

recording a profile representative of light reflection and light absorption of the third type of print medium; and referencing said memory as a look-up table for identifying the profile of the third type of print medium.

9. A method for determining a multi-pick feet of cut sheet print media, the method comprising:

transporting a print medium along a paper path of a hard copy apparatus structure including a lower paper guide including a reflective element and a non-reflective element, the lower paper guide positioned subjacently to a transmissive sensor;

beaming transmissive light through the print medium;

impinging the transmissive light onto the reflective element;

impinging the transmissive light onto the non-reflective element;

sensing a reflected light from the reflective element and the non-reflective element;

recording data representative of light reflection and light absorption;

storing first data representative of media thickness and transmissivity of a single sheet of a known print medium;

storing second data representative of media thickness and transmissivity of at least two stacked sheets of the known print medium;

recording third data representative of the print medium thickness and transmissivity; and comparing said third data to said fist and second data.

10. A print media sensor device, comprising:

a light emitter positioned in a linear transport region of a paper path and directing a light beam across the paper path, the light beam having predetermined intensity and wavelength for penetrating a sheet of print media in said paper path;

a reflective element and a non-reflective element positioned in the linear transport region of the paper path, the reflective element and the non-reflective element supported in a stationary orientation relative to the light emitter and aligned with the light emitter such that said light beam is received by the reflective element and the nonreflective element after passing through the sheet of print media in said paper path; and a light detector positioned in the linear transport region of the paper path and providing an output signal indicative of thickness and transmissivity of the sheet of print media.

11. The device as set forth in claim 10 wherein said output signal further comprises a first level when no print media is interrupting the light beam, a second output signal indicative of the sheet of print media interrupting the light beam, and at least one other signal level indicative of multiple sheets of print media interrupting the light beam.

12. The device as set forth in claim 10 wherein said output signal further comprises a first signal when no print media is interrupting the light beam, a second signal when the sheet of print media is interrupting the light beam over a reflective surface, and a third signal when the sheet of print media is interrupting the light beam over an absorptive surface.

13. The device as set forth in claim 12 further comprising:

the light emitter mounted to a transport, the transport powered for scanning said light beam across the paper path wherein the reflective element and the non-reflective element are mounted transverse to said paper path such that the sheet of print media passes between said light emitter and said effective element and said non-reflective element.

14. The device as set forth in claim 13 wherein the light emitter further comprises:

an LED optical emitter.

* * * * *

UNITED STATES PATENT AND TRADEMARK OFFICE
CERTIFICATE OF CORRECTION

PATENT NO. : 6,794,668 B2
DATED : September 21, 2004
INVENTOR(S) : Arthur H. Barnes It is certified that error appears in the above-identified patent and that said Letters Patent is hereby corrected as shown below:

Column 4,
Line 13, after "105" insert -- shown including light emitter 121 and light detector 122, --
Line 16, after "zone" insert -- 102 --

Column 6,
Line 14, after "wherein" delete -- the step of --

Signed and Sealed this

Fifth Day of April, 2005

JON W. DUDAS
*Director of the United States Patent and Trademark Office*